United States Patent [19]
Azzopardi et al.

[11] Patent Number: 5,997,943
[45] Date of Patent: Dec. 7, 1999

[54] COMPOUND FOR A NON-WETTABLE COATING, PROCESS FOR TREATMENT OF GLASS WITH THE AID OF THE COMPOUND AND PRODUCTS OBTAINED

[75] Inventors: Marie-Jose' Azzopardi; Xavier Talpaert, both of Paris; Fabienne Gauthier, Saint Pere sur Loire, all of France

[73] Assignee: Saint-Gobain Vitrage, Courbevoie, France

[21] Appl. No.: 08/831,942

[22] Filed: Apr. 2, 1997

[30] Foreign Application Priority Data

Apr. 2, 1996 [FR] France ................................. 96 04095
Jun. 6, 1996 [FR] France ................................. 96 06972

[51] Int. Cl.$^6$ ............................. B05D 5/06; B32B 17/06
[52] U.S. Cl. ........................... 427/167; 427/165; 427/384; 427/387; 427/389.7; 427/402; 427/407.2; 428/429; 428/447; 428/448
[58] Field of Search ..................................... 427/165, 167, 427/384, 287, 387, 266, 402, 407.2, 389.7; 106/2, 13; 428/429, 447, 448

[56] References Cited

U.S. PATENT DOCUMENTS 5,266,222  11/1993  Willis et al. ...................... 252/49.006
5,556,667  9/1996   Teranishi et al. ...................... 427/164

FOREIGN PATENT DOCUMENTS 0 548 775   6/1993   European Pat. Off. .
0 657 393   6/1995   European Pat. Off. .
0 738 771   10/1996  European Pat. Off. .
2 674 862   10/1992  France .
WO-A-96
  06895     3/1996   WIPO .

Primary Examiner—Janyce Bell
Attorney, Agent, or Firm—Oblon, Spivak, McClelland, Maier & Neustadt, P.C.

[57] ABSTRACT

A composition for coating can be made by mixing a fluoroalkoxysilane containing an alkoxy moiety directly bonded to a silicon atom, an aqueous solvent system, and a catalyst. The composition can be used to form a hydrophobic and oleophobic layer on a substrate.

10 Claims, No Drawings

COMPOUND FOR A NON-WETTABLE COATING, PROCESS FOR TREATMENT OF GLASS WITH THE AID OF THE COMPOUND AND PRODUCTS OBTAINED

BACKGROUND OF THE INVENTION

1. Field of the Invention

This invention relates to a composition for a non-wettable coating and its application on a substrate. It also relates to the various products prepared from the composition. More specifically, it relates to the manufacturing process for glass provided with a non-wettable coating.

2. Description of the Background

The wettable nature of a substrate referred to the fact that polar or non-polar liquids adhere to the substrate and form a bothersome film. Wettability means the tendency of the substrates to retain frost, as well as dust and stains of all types, fingerprints, dirt, insects, etc.

The presence of water, frost and/or stains is detrimental to the appearance of the substrate, a possible reduction in transparency of the substrate, as well as an impairment of vision through the substrate. The latter are particularly bothersome when the substrate is glass used in vehicles.

Different types of non-wettable coatings are known, including a non-wettable layer obtained from fluorous organosilanes. The layer can be is obtained by applying on the surface of a substrate a solution containing fluorous organosilanes in a non-aqueous organic solvent. As a non-aqueous organic solvent, document 492,545 cites, in particular, n-hexadecane, toluene, xylene, etc. These solvents are particularly appropriate for a fluorochlorosilane. It is also possible, according to this document, to use a methyl or ethyl alcohol as a solvent when the fluorous silane is a fluoroalkoxysilane. However, it is necessary to deposit the layer in the absence of moisture, which is difficult to implement.

SUMMARY OF THE INVENTION

An object of the invention is a composition for coating a substrate, where the wettability properties of the coating are satisfactory and for which the deposition process is simple and practical.

Another object of the invention is a composition deposited on the surface of a substrate in the presence of moisture, particularly in the ambient atmosphere with no moisture restrictions.

These objects are provided by a hydrophobic and oleophobic composition comprising at least one fluoroalkoxysilane, the alkoxy moieties of which are directly bonded to a silicon atom, an aqueous solvent system and at least one catalyst selected from an acid and/or a Bronsted base.

In addition to the hydrophobic, oleophobic, anti-rain, anti-frost, anti-stain, anti-dirt, etc. effects obtained by this composition, other advantages are gained when underlying functional layers are included, or with stacks. This case refers in particular to application A1-0 682,463 describing a glass comprising a glass substrate, an anti-reflection, low-emission and/or conducting functional stack, overlaid with a hydrophobic and oleophobic layer.

In such a configuration, the composition of the invention protects the functional stack from climatic conditions, or a possible chemical or hydrolytic assault. In the latter case, there is an improvement in holding quality in warm, moist atmospheres and by superior results in neutral saline fog tests. An increase in durability is obtained, or even a guaranteed quasi-permanence of the underlying anti-reflection or low-emission function.

The anti-adherent property of the hydrophobic and oleophobic coating according to the invention is particularly important when it overlays an anti-reflection layer or stack, since anti-reflection layers and stacks are typically plagued by the presence of undesirable markings on their surfaces.

Aqueous solvent system for use in the present invention are any type of solvent capable of both solubilizing and hydrolyzing the fluoroalkoxysilane. Preferably, it is a mixture of two components: a solvent capable of solubilizing the fluoroalkoxysilane and optionally a catalyst, and an aqueous compound capable of hydrolyzing the silane in the presence of a catalyst. An alkanol, for example an alkanol of low molecular weight, such as methanol, ethanol, butanol or isopropanol, is preferred as a solvent. An aqueous compound is a compound capable of releasing $H^+$ (protons), preferably water.

The fluorous silanes used according to the invention comprise a hydrolyzable moiety, capable of forming silanols with the formula Si—OH. The nature of this moiety affects the speed of hydrolysis of the silane. It is selected so as to allow the deposition of the compound on the substrate in an ambient atmosphere, preferably an alkoxy moiety.

The fluorine groups of the alkoxysilane impart to the layer obtained a particularly marked hydrophobia and oleophobia. The fluorine groups further impart a good resistance to ultraviolet light. The fluoroalkoxysilanes used according to the invention are preferably perfluoroalkoxysilanes having the formula:

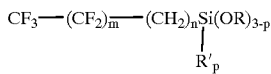

with:
m=0 to 15
n=1 to 5
p=0, 1, 2
R is an alkyl
R' is an alkyl or H

The alkyl of R or R' may be $C_{1-100}$ or $C_{1-30}$. Each R and R' may be selected independently.

The organosilane carbon chain is preferably relatively long. Preferably, the number of —$CF_2$— moieties is larger than the number of —$CH_2$— moieties in order to impart a greater fluorine density on the outside: m is preferably at least 2×n.

The fluoroalkoxysilane are preferably selected from the following alone or in combination:

A perfluorotrialkoxysilane, having the formulas:

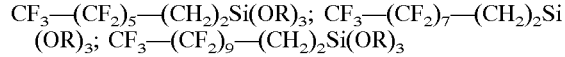

Where R is an alkyl, preferably methyl or ethyl; a perfluorodialkoxysilanes having the formulas:

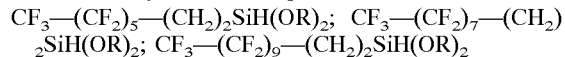

where R is an alkyl, preferably methyl or ethyl.

The proportion of fluoroalkoxysilane in the composition may range from 0.05 to 5%, by weight with respect to the composition, preferably, 1 to 3% by weight.

The proportions of the various components of the composition affect the wettability of the coating. The proportion of the aqueous compound, for example water, with respect to the solvent itself, for example an alcohol, ranges from 3 to 20% by volume, and preferably is on the order of 10% by volume. Thus, it is possible that the alkoxysilanes present in an aqueous solvent system may begin to hydrolyze, forming silanols capable of reacting with the reactive groups on the surface of the substrate. An excessively large proportion of hydrolyzed silanes may lead to homopolymerization. The number of alkanols capable of reacting with the surface of the substrate is then reduced. Likewise, an excessively small proportion of hydrolyzed silanes may lead to an excessively small number of silanes affixed to the surface of the substrate.

A catalyst catalyzes the hydrolysis reaction. The catalyst may be a Bronsted acid and/or base; it is capable of releasing an $H^+$ or an $OH^-$ ion, for example, hydrochloric or acetic acid. The proportion of catalyst in the composition also affects the wettability nature of the coating, and preferably is present in from 0.005 and 20% by weight with respect to the composition, and more preferably, on the order of 10% by weight with respect to the composition.

The coating is obtained through reaction of the hydrolyzed alkoxysilanes with reactive groups on the surface of the substrate, forming a covalent bond. The overall structure of the layer is, for an organosilane, covalent bonding at the point of fixation on the surface of the substrate, and one or two covalent bonds with neighboring organosilane molecules, through other hydrolyzable moieties.

The thickness of the layer obtained ranges from 10 to 150 angstroms, preferably 10 to 100 angstroms. The layer preferably does not impair the transparency of, or vision through, the substrate.

The composition according to the invention is applied on at least one portion of a surface of a substrate, comprising, in particular OH groups capable of reacting with the hydrolyzed silane of the compound. The substrate may be made of a mineral glass, a plastic material, such as polycarbonate for example, or a base coated with at least one mineral and/or inorganic layer. Examples of mineral an/or inorganic layers include functional layers such as anti-streaking, anti-abrasion, anti-reflection layers, decorative and low-emission layers, as indicated above. These layers may also be organic.

The composition according to the invention also may be deposited on a layer which is at least partially degraded. This degradation may be due, for example, to natural aging or to a mechanical or chemical abrasion. Abrasion may be due to the rubbing of windshield wipers or to the impact of rain, hail, or shock. As the surface on a degraded layer is as effective as the initial surface, it is not necessary to prepare the surface, such as with abrasion, or polishing, prior to deposition of the composition of the invention.

Nonetheless, the durability of the layer according to the invention, preferably, may be improved by a preliminary treatment of the substrate with a priming compound of the type $SiX_4$, where X is a hydrolyzable group, for example chloride or alkoxy. X may be other halides, such as bromine. The alkoxy may have 1–100 carbon atoms. Priming increases the reactivity of the glass, which results in an improvement in attachment of the fluorous silane. In addition, the priming disorganizes the fluorous layer and thus makes it possible to form it with a greater thicknesses, at least equal to 100 angstroms, without, however, exceeding 500 angstroms: it does not refer to a monomolecular layer. The increase thus obtained in the amount of fluorine deposited results in an increased durability under conditions of exposure to ultraviolet radiation. Moreover, at the above-mentioned thickness values for the fluorous layer, a scratch in the layer is not visible to the naked eye.

The invention also relates to the process for manufacture of glass provided with a hydrophobic and oleophobic coating.

The process for manufacture of the glass more specifically comprises the following steps:
preparing the composition capable of forming the hydrophobic and oleophobic layer,
preparing, optionally, the priming compound,
depositing the composition on at least a portion of the surface of the glass which, optionally, has been treated with the priming compound.

The preparation of the compound comprises, in particular, mixing of a fluoroalkoxysilane of the invention with an aqueous solvent system and at least one catalyst. This mixing may be performed in the presence of moisture, in particular in the ambient atmosphere. The product obtained is a reactive solution, for example, for 24 hours after preparation. This solution is deposited on at least a portion of the glass, preferably from 10 minutes to one hour after its preparation. Deposition is performed by placing the glass in contact with the solution, by any means, for example by casting, spraying, centrifugation, immersion, dipping, by means of a coating roller or a brush or, preferably, by wiping. The substrate may be at room temperature or heated to a temperature of up to 300° C. Beyond 300° C., there is a risk that the layer will be degraded.

The priming treatment may be accomplished by using the same deposition process as that used for the deposition of the hydrophobic and oleophobic layer, and by using the same aqueous solvent and catalyst system. The priming compound may contain from 0.001 to 5% by weight of $SiX_4$. The treatment with the priming compound has the effect of increasing the number of reactive sites (hydroxylated sites) on the surface of the substrates.

The glass contemplated according to the invention is glass comprising mineral and/or organic glass. It is used, in particular, in the aeronautical, railroad or automobile areas. It also can be used in construction or in interiors, for example, as decorative panels, for furnishings, etc. The substrate on which the compound of the invention is capable of being applied moreover may be made up of any material comprising surface hydroxylated groups, such as glass products coated or not coated with mineral and/or inorganic, ceramic, vitroceramic layers (for example, heating plates), vitrified products, concrete or flagstones. The invention is applicable in areas as different as those of glazing, electric domestic appliances, building (windows), cooking utensils, sanitary fixtures (washbasin, bathtub), construction materials, etc.

The surface of the glass to be coated must be clean. The cleanliness of the glass determines the number of reactive sites on the substrate capable of reacting with the hydrolyzed alkoxysilane groups. Its purpose is to avoid the presence of any contaminations, essentially organic, adsorbed on the surface of the substrate and capable of resisting reaction with the hydrolyzed alkoxysilanes on the reactive sites of the substrate. The surface of the glass is cleaned beforehand, for example with the aid of a tensioactive agent.

The substrates prepared with the layers of the invention are both hydrophobic and oleophobic. They have good resistance to ultraviolet radiation, chemical assaults and mechanical abrasion. They are used advantageously as anti-rain, anti-frost, anti-stain, anti-contaminant, anti-dirt substrates, etc. They are used particularly on glass in land and aeronautical vehicles or for buildings.

DETAILED DESCRIPTION OF THE INVENTION

The following nonrestrictive examples illustrate the characteristics and advantages of the invention:

Example 1 illustrates the non-wettable nature of the layer according to the invention;

Example 2 is a comparative example for Example 1;

Example 3 illustrates the resistance to abrasion of an embodiment of the invention;

Example 4 is a comparative example for Example 3; and

Examples 5a and 5b illustrate a preliminary treatment of the substrate with a priming compound.

The resistance to abrasion of the layer is measured by the so-called "windshield wipes" test. The samples are subjected to the action of a wiper blade approximately 50 cm long and exerting a force of 45 newtons on the sample. After a given number of forward and backward motions of the wiper blade, the angle of contact of a drop of water is measured.

EXAMPLE 1

Four samples of float silico-sodo-calcareous glass were cleaned.

This sample was treated with a solution containing a mixture of perfluorotrialkoxysilanes with the formulas:

$$CF_3-(CF_2)_5-(CH_2)_2Si(OC_2H_5)_3;$$

$$CF_3-(CF_2)_7-(CH_2)_2Si(OC_2H_5)_3;$$

$$CF_3-(CF_2)_9-(CH_2)_2Si(OC_2H_5)_3$$

in an aqueous solvents system comprising ethanol and water, and a catalyst (acetic acid). The solution is applied by wiping. Only the proportions of these different components vary according to the samples. Ninety-five percent ethanol is used. In the following table, the proportions of 95% alcohol have been converted into corresponding percentages of pure alcohol and water. The hydrophobia of the layer thus formed is quantified by measuring the angle of contact θ of a drop of water on the layer. All amounts are volumne percents, here and in the other Examples.

The results are as follows:

| Sample | % pure ethanol | % water | % acetic acid | % silane | θ water |
|---|---|---|---|---|---|
| 1 | 85.5 | 4.5 | 10 | 0.1 | 90° |
| 2 | 85.5 | 4.5 | 10 | 3 | 105–110° |
| 3 | 76 | 14 | 10 | 0.1 | 100–105° |
| 4 | 76 | 14 | 10 | 3 | 105–110° |

It is considered that the non-wettable nature of the layer is satisfactory when the initial angle of contact of a drop of water on said layer is at least of 90°.

This example illustrates the hydrophobic nature of the layer obtained.

EXAMPLE 2—COMPARATIVE EXAMPLE

This example is a comparative example for Example 1.

Four samples were treated in the same manner as in Example 1, except that the compositions used did not comprise any catalyst. The proportions of the components of the solvent system also vary. The ethanol used is 95% ethanol. In the table below, the proportions of 95% alcohol have been converted into corresponding percentages of pure alcohol and water.

The results are as follows:

| Sample | % pure ethanol | % water | % silane | θ water |
|---|---|---|---|---|
| 1 | 95 | 5 | 0.1 | 61–70° |
| 2 | 95 | 5 | 3 | 56–89° |
| 3 | 85.5 | 14.5 | 0.1 | 40–70 |
| 4 | 85.5 | 14.5 | 3 | 70–80 |

The non-wettability nature of the layers obtained is not fully satisfactory: the angles of contact of a drop of water on the layer are less than 90°.

EXAMPLE 3

A sample of float glass of the silico-sodo-calcareous type was given four successive treatments with a solution identical to that used to treat sample No. 4 in Example 1. The sub-layer on which the compound of the invention was deposited by wiping was, each time, degraded by the so-called "windshield-wiper" test.

The results are the following:

| | Wettability of the sub-layer | | Wettability of the layer obtained | |
|---|---|---|---|---|
| | θ | Number of windshield cycles used to degrade the layer | Initial θ | θ after the windshieid-wiper test |
| 1st treatment | — | — | 105–110° | 60° (50,000 cycles) |
| 2nd treatment | 60° | 50,000 | 100–105° | 65° (70,000 cycles) |
| 3rd treatment | 65° | 70,000 | 110° | 70° (100,000 cycles) |
| 4th treatment | 70° | 100,000 | 115° | 70° (100,000 cycles) |

It is considered that the resistance to abrasion of the layer is satisfactory if the angle of contact of a drop of water on the layer is in excess of 60° after the windshield-wiper test.

This example illustrates the improved resistance of the layer obtained on a sub-layer which has been at least partially degraded.

Regenerations on layers previously degraded with the aircraft windshield-wiper test show holding qualities at least equivalent, and in some cases superior, to those of the initial layer. Initially, the contact angle of water θ≈60° after 50,000 aircraft windshield-wiper cycles. After 3 or 4 cycles of abrasion with an aircraft windshield wiper and reapplication of the anti-rain layer, the contact angle of water θ≈60° is obtained after 100,000 aircraft windshield-wiper cycles.

EXAMPLE 4—COMPARATIVE EXAMPLE

This example is a comparative example for Example 3. A sample of float glass of the silico-sodo-calcareous type was twice treated with a solution containing 0.5% by volume of a fluorochlorosilane with the formula: $CF_3-(CF_2)_7-(CH_2)_2SiCl_3$ in a nonaqueous solvent such as decane. As in Example 3, the first layer obtained by the first treatment is degraded with the aid of the so-called "windshield-wiper" test prior to depositing the second layer.

The results are as follows:

|  | Wettability of the sub-layer | | Wettability of the layer obtained | |
| --- | --- | --- | --- | --- |
|  | θ | Number of windshield cycles used to degrade the layer | Initial θ | θ after the windshield-wiper test |
| 1st treatment | — | — | 100–105° | 70° (50,000 cycles) |
| 2nd treatment | 65–80° | 50,000 | 95–110° | 55° (70,000 cycles) |

This example illustrates the poor resistance to abrasion of a layer of the prior art deposited on a sub-layer at least partially degraded: the angle of contact of a drop of water on a layer which has undergone 50,000 windshield-wiper cycles is less than 60° on the average.

EXAMPLES 5a AND 5b

The procedure used was the same as in sample 4 of Example 1, except that the substrate was treated beforehand with a priming compound containing 76 parts pure ethanol, 14 parts water, 10 parts acetic acid and 1 part type $SiX_4$ silane (one part $Si(OCH_3)_4$, for Example 5a and one part $Si(OC_2H_5)_4$ for Example 5b).

The results are as follows:

| Example | Initial θ | θ after the windshield-wiper test |
| --- | --- | --- |
| 5a | 105° | 100° after 250,000 cycles |
| 5b | 110° | 90° after 100,000 cycles |

Compared to the first treatment in the table for Example 3, a significant improvement is noted in the holding quality of the hydrophobic and oleophobic layer in the windshield-wiper test.

Obviously, numerous modifications and variations of the present invention are possible in light of the above teachings. It is therefore to be understood that within the scope of the appended claims, the invention may be practiced otherwise than as specifically described herein.

The priority documents of the present application, French Patent Application No. 96/04095 filed on Apr. 2, 1996, and French Patent Application No. 96/06972 filed on Jun. 6, 1996, are hereby incorporated by reference.

What is claimed is:

1. A process for coating a substrate, comprising:
   applying a primer to a substrate, said primer prepared by mixing
   (a) $SiX_4$,
   (b) an aqueous solvent system, and
   (c) a catalyst,
   wherein each X is independently selected from the group consisting of halide and alkoxy;
   applying a coating composition prepared by mixing
   (i) a fluoroalkoxysilane containing an alkoxy moiety directly bonded to a silicon atom,
   (ii) an aqueous solvent system,
   (iii) a catalyst.

2. The process of claim 1, wherein the catalyst in the coating composition is selected from the group consisting of a Bronsted acid and a Bronsted base.

3. The process of claim 1, wherein the aqueous solvent system in the coating composition comprises an alcohol and water.

4. The process of claim 3, wherein said alcohol is selected from the group consisting of methanol, ethanol, butanol, isopropanol and mixtures thereof.

5. The process of claim 3, wherein the water is present an amount of 3 to 20% by volume, based on said alcohol.

6. The process of claim 1, wherein said fluoroalkoxysilane has the formula:

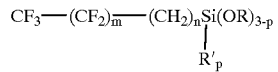

wherein m=0 to 15;

n=1 to 5;

p=0, 1, 2;

each R is an alkyl, each R' is an alkyl or H.

7. The process of claim 1, wherein the step of applying said coating composition is performed at most 24 hours after preparation of said coating composition.

8. The process of claim 1, wherein the substrate is glass.

9. A coated substrate obtained by the process of claim 8.

10. A coated substrate obtained by the process of claim 1.

* * * * *